United States Patent [19]
Nelson et al.

[11] Patent Number: 5,591,878
[45] Date of Patent: Jan. 7, 1997

[54] CATALYZED PROCESS FOR PRODUCING METAL CARBOXYLATES FOR USE AS ANIMAL FEED SUPPLEMENTS

[75] Inventors: Christopher E. Nelson, Des Moines; Douglas H. Catron, Ames, both of Iowa

[73] Assignee: Kemin Industries, Inc., Des Moines, Iowa

[21] Appl. No.: 531,193

[22] Filed: Sep. 19, 1995

[51] Int. Cl.$^6$ .................. C07F 15/06; C07F 11/00; C07F 13/00
[52] U.S. Cl. .................. 556/49; 556/61; 556/147
[58] Field of Search .................. 556/49, 61, 147

[56] References Cited

U.S. PATENT DOCUMENTS

| | | | |
|---|---|---|---|
| 3,755,391 | 8/1973 | Bertrand et al. | 260/429 R |
| 4,101,567 | 7/1978 | Fitzmaurice et al. | 260/438.5 R |
| 4,315,927 | 2/1982 | Evans | 424/245 |
| 4,636,572 | 1/1987 | Hudson et al. | 556/2 |
| 4,700,000 | 10/1987 | Merkel et al. | 562/606 |

*Primary Examiner*—Porfirio Nazario-Gonzalez
*Attorney, Agent, or Firm*—Welsh & Katz, Ltd.

[57] ABSTRACT

A catalyzed process is disclosed for producing a polyvalent metal $C_2$–$C_3$ carboxylate having the formula $M(CH_3(CH_2)_xCOO^-)_y$, wherein M is the polyvalent metal cation that is manganese ($Mn^{+2}$), cobalt ($Co^{+2}$), or chromium ($Cr^{+3}$), x is zero or 1 and y is an integer equal to the cationic charge of M. The polyvalent metal $C_2$–$C_3$ carboxylate is prepared by admixing (i) a dry polyvalent metal compound that is an oxide, hydroxide or carbonate of $Mn^{+2}$, $Co^{+3}$ or $Cr^{+3}$, (ii) an anhydrous $C_2$–$C_3$ carboxylic acid, and (iii) a catalytic agent at a relative molar ratio of about 1:2–10:0.01–3 in the absence of an added solvent or other diluent to form a reaction mixture. The reaction mixture is heated to complete the reaction, remove the produced water and about 80 percent of the unreacted carboxylic acid. The product in residual carboxylic acid is solidified, ground and the product is recovered. The metal carboxylates can be used as biologically available and economical sources of trace metal ions for supplementation in animal diets.

11 Claims, No Drawings

CATALYZED PROCESS FOR PRODUCING METAL CARBOXYLATES FOR USE AS ANIMAL FEED SUPPLEMENTS

DESCRIPTION

1. Technical Field

The present invention relates to a catalyzed process for producing metal carboxylates, and more particularly polyvalent metal acetate and propionate salts that are used for trace metal supplementation of animal feed.

2. Background of the Invention

Trace elements are essential for the nutrition of animals, playing important roles in many biochemical and physiological processes. These elements include metals that form polyvalent cations such as zinc, copper, iron, manganese, cobalt, chromium, and molybdenum. All but molybdenum have been shown to be deficient in some natural feed ingredients, necessitating the use of supplements to make the diet nutritionally complete.

Several chemical forms of trace metals are available for supplementation of animal diets including the inorganic salts of the trace metal, metal-amino acid complexes, metal-amino acid chelate complexes, metal-proteinate complexes, and metal-polysaccharide complexes (Official Publication of American Feed Control Officials, 1995, pages 209-210). U.S. Pat. No. 4,315,927 also discloses the use of a metal carboxylate complex, zinc picolinate, as an animal feed supplement. All of the complexes result from the complexing of a soluble metal salt with the amino acid, chelate, proteinate, polysaccharide, or carboxylic acid.

The salts of acetic acid, including zinc acetate, manganese acetate, and cobalt acetate, have been also been approved for use as animal feed supplements (21 CFR 582.80). Zinc acetate can be prepared in the conventional manner discussed below.

U.S. Pat. No. 4,700,000 discloses that carboxylic acid salts are conventionally synthesized by reacting a carbonate, hydroxide, or oxide with a concentrated or dilute carboxylic acid. The carboxylic acid is in solution as denoted by the terms "concentrated" and "dilute". The carbonate, hydroxide, or oxide are bases that react with the aqueous carboxylic acid to form a carboxylic acid salt in an acid-base neutralization reaction. The reactants in the conventional method are therefore in an aqueous solution.

U.S. Pat. No. 4,700,000 also discloses that calcium propionate is prepared by reacting propionic acid with calcium hydroxide in an aqueous solution. After concentration and crystallization, the product is separated from the solution by filtration, decantation, or centrifugation, dried and ground. U.S. Pat. No. 4,315,927 discloses that the zinc picolinate complex is prepared by adding picolinic acid to an aqueous solution of a water-soluble metal salt, zinc sulfate. The product is precipitated, purified by recrystallization, recovered and dried by freeze-drying.

Similar starting compounds of manganese and cobalt (the hydroxides, oxides or carbonates) are not reactive enough to form manganese or cobalt acetate using the above conventional synthesis. Rather, manganese and cobalt acetate are formed by reaction of the appropriate metal oxide with propionaldehyde. However, the aldehydes used in those reactions are volatile and have flash points below zero degrees C.

One of the disadvantages of a conventional aqueous solution method of preparation is that it is not an economical method for certain transition elements particularly the desired trace metals, iron ($Fe^{+2}$ or $Fe^{+3}$), manganese ($Mn^{+2}$), cobalt ($Co^{+2}$), and chromium ($Cr^{+3}$) under normal conditions. The carboxylic acid and the basic metal compound react to a limited extent, but the reaction does not go to completion in a reasonable time period. Another disadvantage is that the use of an aqueous solution necessitates the separation of the precipitated product from the solution, and drying of the recovered product. Still another disadvantage of a conventional method is that in some cases, the polyvalent metal cation-containing base is sparingly soluble or insoluble in water.

It would therefore be a benefit if an economical means of production were available in which the acid-base reaction goes to completion, the product were more readily obtained and the solubility or lack of solubility of the polyvalent metal cation-containing base is of little or no concern. The detailed description that follows describes a synthetic process that to a great extent overcomes the before-discussed disadvantages.

BRIEF SUMMARY OF THE INVENTION

The present invention relates to a catalyzed process for producing a polyvalent metal salt of a carboxylic acid (a metal carboxylate) having the formula, $M(CH_3(CH_2)_xCOO^{13})_y$, wherein M is the polyvalent metal cation, manganese ($Mn^{+2}$), cobalt ($Co^{+2}$), or chromium ($Cr^{+3}$), x is zero or 1 so that an acetate or propionate salt is made, and y is an integer equal to the cationic charge of M.

The process involves admixing (i) an anhydrous $C_2$–$C_3$ carboxylic acid, propionic acid or acetic acid, with (ii) a dry, basic polyvalent metal compound that is an oxide, hydroxide or carbonate of an above polyvalent metal cation ($Mn^{+2}$, $Co^{+2}$ or $Cr^{+3}$) and (iii) a catalytic agent. The catalytic agent is an alkali metal or alkaline earth metal salt of the carboxylic acid, or an alkali metal or an alkaline earth metal compound (oxide, hydroxide or carbonate) that reacts with the carboxylic acid to Form a metal salt of the carboxylic acid. The alkali metal or alkaline earth metal compound acts as a pre-catalyst in that on admixture with the carboxylic acid a catalyst is formed, and the metal salt of the carboxylic acid acts as a catalyst for the reaction. The three ingredients are admixed in the absence of added solvent or other diluent at a relative molar ratio of about 2–10:1:0.01–3, respectively, and preferably at about 5:1:1, to form an exothermic reaction mixture that produces water as a product and the desired polyvalent metal cation $C_2$–$C_3$ carboxylate. Carbon dioxide is also formed when a polyvalent metal cation carbonate is used as a reactant.

The reaction mixture is heated to reflux while continually removing formed water produced by the neutralization reaction to form a solution of the polyvalent metal cation carboxylate and the catalyst in excess carboxylic acid. The excess carboxylic acid is also removed until about 80 percent of the remaining (unreacted) carboxylic acid is removed. The solution is cooled to solidify, and then ground and warmed to release the residual carboxylic acid that is then separated from the product polyvalent metal ion carboxylate. The final product contains the polyvalent metal cation carboxylate and the catalyst (alkali metal or alkaline earth metal ion carboxylate) that is dry.

The present invention has several benefits and advantages. One benefit of this invention is that it provides a catalyzed process for preparing polyvalent metal cation carboxylates with polyvalent metal cations that cannot be economically prepared by the conventional aqueous solution method. Another benefit is that the reaction of the starting dry, basic polyvalent metal compound can be driven to completion. An advantage of this invention is that it provides a catalyzed process for making polyvalent metal cation carboxylate that is low in cost and easy to perform on a large commercial scale without the use of low flash point reactants. Still further advantages of the invention will be apparent to a worker of ordinary skill from the description that follows.

DETAILED DESCRIPTION OF THE INVENTION

The present invention relates to the preparation of a polyvalent metal cation carboxylate using a catalyzed process. A polyvalent metal cation $C_2$–$C_3$ carboxylate has the formula, $M(CH_3(CH_2)_xCOO^-)_y$, wherein M is the polyvalent metal cation, manganese ($Mn^{+2}$), cobalt ($Co^{+2}$), or chromium ($Cr^{+3}$), and x is zero or 1 and y is an integer equal to the cationic charge of M. The contemplated carboxylates are thus acetates ($C_2$) and propionates ($C_3$). The source of the metal cation, M, is a polyvalent metal compound that is an oxide, hydroxide or carbonate of manganese, cobalt or chromium, preferably manganese carbonate, cobalt carbonate or chromic oxide.

The following description of the present invention illustrates a process for preparing polyvalent metal cation propionates, but the described process is also useful for the preparation of polyvalent metal cation acetates with the use of acetic acid instead of propionic acid.

Manganese propionate, cobalt propionate or chromic propionate is prepared by admixing pure, anhydrous propionic acid with an oxide, hydroxide or carbonate of the polyvalent metal cation, $Mn^{+2}$, $Co^{+2}$ or $Cr^{+3}$, preferably manganese carbonate, cobalt carbonate or chromic oxide and a catalytic agent. The catalytic agent is a pre-catalyst or a catalyst.

The pre-catalyst is an alkali metal or alkaline earth metal compound, preferably sodium hydroxide, that reacts with propionic acid to form a corresponding metal salt of the propionic acid, preferably sodium propionate. The catalyst is an alkali metal or alkaline earth metal salt of the propionic acid, and is required for the reaction to go to completion in a useful time period, such as less than one day at reflux temperature and one atmosphere of pressure.

It is to be understood that an alkaline earth metal cation (e.g., $Ca^{+2}$, $Mg^{+2}$ or $Ba^{+2}$) is polyvalent as are $Mn^{+2}$ and $Co^{+2}$. However, the term "polyvalent metal cation" is reserved herein for $Mn^{+2}$, $Co^{+2}$ and $Cr^{+3}$.

The term catalyst is used interchangeably with any alkali metal or alkaline earth metal salt of propionic acid, preferably sodium propionate. The term pre-catalyst is used interchangeably with any alkali metal or alkaline earth metal compound that reacts with propionic acid to form an alkali metal or alkaline earth metal salt of propionic acid, preferably sodium hydroxide.

The polyvalent metal cation, the propionic acid and the catalytic agent are used at the relative molar ratio of about 1:2–10:0.01–3, with a preferred molar ratio of about 1:5:1, respectively. The propionic acid (acetic acid) is present in excess, e.g., up to about 2 to 10 times the molar amount of the polyvalent metal cation. The excess propionic acid (or acetic acid) serves as a dispersing agent and heat exchange medium for the reactants. The catalytic agent can be used in trace amounts, but preferably is present in the same molar amount as the polyvalent metal cation; i.e., at one-half the normality of the divalent metal cation. The greater amount of catalytic agent results in shorter reaction time but a lower yield of polyvalent metal cation propionate relative to regenerated catalyst.

When used in this reaction, both the propionic acid and polyvalent metal compound are anhydrous. That is, both are substantially free of water so that neither contains more than a total of about 5 weight percent water or an aggregate of about 10 weight percent water. The propionic acid is anhydrous, containing less than about 0.5 weight percent water. The propionic acid more preferably contains at most about 0.1 to about 0.2 weight percent water. The polyvalent metal compound preferably has no waters of crystallization, as is the case with the usually reported and available forms of those polyvalent metal compounds. The polyvalent metal compound is utilized in a dry, particulate form. The use of a relatively small particle size is preferred to help assure contact of the reactants and subsequent reaction. Thus, a powder form is preferred.

Propionic acid melts at about −23° to −24° C. and boils at about 142° C. (about 288° F.) at one atmosphere. The propionic acid is utilized in the reaction in its liquid form. Propionic acid forms an azeotrope with water that boils at about 100° C. (about 212° F.) and contains about 18 weight percent propionic acid. As a consequence of the formation of the azeotrope and the relatively low boiling point of that mixture, some propionic acid can be and is lost at higher reaction temperatures as water is removed from the reaction mixture. Acetic acid melts at about 17° C. and boils at about 118° C. at one atmosphere. Acetic acid forms an azeotrope with water that boils at about 77° C. and contains about 3 weight percent acetic acid.

The catalytic agent is a catalyst; i.e., an alkali metal or alkaline earth metal salt of propionic or acetic acid, or a pre-catalyst; i.e., any alkali metal or alkaline earth metal compound that reacts with propionic or acetic acid to form the corresponding salt. The alkali metal or alkaline earth metal includes, but is not limited to lithium, sodium, potassium, magnesium, calcium and barium. The pre-catalyst is any alkali metal or alkaline earth metal compound including but not limited to the oxide, carbonate, or hydroxide of sodium, potassium, magnesium, calcium, or barium. The preferred pre-catalyst is sodium hydroxide that reacts with propionic acid to form the catalyst, sodium propionate. Sodium hydroxide beads are preferably utilized that are approximately 95 percent pure. The catalytic agent increases the rate of reaction so that the reaction proceeds to completion in approximately 2 to 3 hours.

In this illustration, the propionic acid, the polyvalent metal compound, and the pre-catalyst are admixed together. The reaction unexpectedly occurs without having to dissolve the propionic acid or the polyvalent metal compound in water or suspend the reactants in any other liquid or solid diluent. This is an advantage because the metal compounds used in the present invention are sparingly soluble in water.

The mixture is heated to reflux (about 98°–100°), reaching a reaction mixture temperature of approximately 121° C. The reaction proceeds exothermically according to the following equations:

1)  $MnCO_3 + 3CH_3CH_2COOH + NaOH \rightarrow Mn(CH_3CH_2CO_2)_2 + Na(CH_3CH_2CO_2) + 2H_2O + CO_2$ 2)  $CoCO_3 + 3CH_3CH_2COOH + NaOH \rightarrow Co(CH_3CH_2CO_2)_2 + Na(CH_3CH_2CO_2) + 2H_2O + CO_2$ 3)  $Cr_2O_3 8CH_3CH_2COOH + 2NaOH \rightarrow 2Cr(CH_3CH_2CO_2)_3 + 2Na(CH_3CH_2CO_2) + 5H_2O$ The reaction is maintained at reflux with agitation and by means of additional heat. Water and heat are generated when propionic acid and the polyvalent metal compound are reacted, as is carbon dioxide when a carbonate is used.

The heat of the reaction is insufficient to evaporate the water formed. The water is evaporated with the aid of additional heat and is removed by fractional distillation. Some propionic acid that forms an azeotrope with water is also removed along with the water. The reaction is complete when the temperature of the reaction mixture reaches approximately 180° C., with a distillation head temperature of about 141°–142° C. A solution is obtained of the metal propionate and catalyst in unreacted propionic acid present from the stoichiometric excess, and distillation is continued until about 80 percent of the remaining, unreacted propionic acid is removed. The solution is cooled to solidity, and ground releasing any propionic acid, to obtain the final product. The final product contains the metal propionate and catalyst.

Residual propionic acid is trapped within the crystalline structure of the metal propionate when an above solution is frozen. The mechanical energy input provided during the grinding, the large surface area produced by the grinding and the vapor pressure of the carboxylic acids at ambient temperature enables most of the residual propionic acid to volatilize. The product metal propionate frequently has a small amount of residual carboxylic acid present that is sufficient to impart a slight odor to the product.

In one embodiment of this process, anhydrous propionic acid was mixed with dry manganese carbonate and sodium hydroxide beads to yield greater than 67.67 percent manganese propionate and sodium propionate in 2.5 hours. In comparison, where sodium hydroxide not used, the yield of manganese propionate was less than 1.00 percent after stirring the mixture under vacuum for 48 hours.

A metal propionate produced by an above process is typically and preferably a powder that is itself dry, as defined before, but can clump slightly due to the presence of some residual propionic acid. It is most preferred that the polyvalent metal propionate have an appearance similar to that of commercially available talcum powder.

The polyvalent metal propionates and analogous polyvalent metal acetates produced from an above process are used as sources of trace polyvalent metal ions for supplementation of animal feed. Exemplary feeds that can be supplemented with polyvalent metal propionates include finished feeds of poultry, swine, horses, dairy and beef cattle, goats and sheep.

The following examples are offered to further illustrate but not limit the product and process of the present invention.

EXAMPLE 1

Manganese Propionate

A preparation of manganese propionate was made by combining 155.64 grams of dry manganese carbonate, 501.67 grams of anhydrous propionic acid and 54.17 grams of sodium hydroxide to provide a relative molar ratio of 1:5:1, respectively. The mixture was heated to reflux with constant stirring for 35 minutes. The reaction went to completion in approximately 2.5 hours. Water with some propionic acid was removed by fractional distillation. Heat was increased until the water and 80 percent of the remaining propionic acid liquid had been removed. Carbon dioxide was released through a vented condenser.

The resulting solution of manganese propionate and sodium propionate in residual propionic acid was poured into a flat metal pan and placed in a freezer until solid. After cooling, the solution solidified into dark burgundy "glass". The "glass" was ground releasing the propionic acid to volatilize. A white to slightly pink powder was collected that contained 67.67 percent manganese propionate and 32.3 percent sodium propionate.

EXAMPLE 2

Manganese Propionate

In a reaction vessel, 145.83 grams of manganese carbonate, 328.92 grams of propionic acid and 25.38 grams of sodium hydroxide, a relative molar ratio of 2:7:1 respectively, was combined and heated to reflux. Water was removed from the vessel during the reaction by means of a fractional distillation column. The reaction went to completion after 10 hours, producing a dark burgundy solution from which about 80 percent of the remaining acid was removed. The product solidified at 130° C. The final product contained 80.7 percent manganese propionate and 19.3 percent sodium propionate.

EXAMPLE 3

Cobalt Propionate

A preparation of cobalt propionate was made by combining 85.42 grams of dry cobalt carbonate and 266.60 grams of anhydrous propionic acid and 28.73 grams of sodium hydroxide, a relative molar ratio of 1:5:1, respectively. The mixture was heated to reflux with constant stirring for 35 minutes. The reaction went to completion in approximately 2.5 hours. Water with some propionic acid was removed by fractional distillation. Heat was increased until the water and about 80 percent of the remaining propionic acid liquid had been removed. Carbon dioxide was released through a vented condenser. The resulting solution of cobalt propionate and sodium propionate in residual propionic acid was poured into a flat metal pan and placed in a freezer until cool. After cooling, the solution solidified into a bright pink "glass". The "glass" was ground releasing the propionic acid. A purple powder was collected which consisted of cobalt propionate and sodium propionate.

EXAMPLE 4

Simultaneous preparation of manganese and cobalt propionate

Cobalt propionate and manganese propionate were prepared by combining 19.3 grams of dry cobalt carbonate with 155.3 grams of anhydrous propionic acid and 60.5 grams of sodium hydroxide, a relative molar ratio of 0.893 $Mn^{+2}$:0.107 $Co^{+2}$:5 propionic acid:1 sodium hydroxide. The mixture was heated to reflux. Water along with some propionic acid was removed by fractional distillation. Heat was increased until the water and about 80 percent of the remaining propionic acid liquid had been removed. Carbon dioxide was released through a vented condenser. The resulting composition of manganese propionate, cobalt propionate and sodium propionate dissolved in residual propionic acid was poured into a flat metal pan and placed in a freezer until cool. After cooling, the solution solidified into a bright pink "glass". The "glass" was ground releasing the propionic acid. A purple powder was collected which that contained manganese propionate, cobalt propionate and sodium propionate.

EXAMPLE 5

Chromium (III) Propionate

A preparation of chromium propionate is made by combining 151.99 grams of chromic oxide and 444.48 grams of dry propionic acid and 40.01 grams of sodium hydroxide. The mixture is heated to reflux with constant stirring. Water with some propionic acid is removed by fractional distillation. Heat is increased until the water and about 80 percent of propionic acid liquid is removed. The resulting composition of chromium propionate and sodium propionate dissolved in propionic acid is poured into a flat metal pan and placed in a freezer until cool. After cooling, the solution solidifies into a "glass" The "glass" is ground releasing the propionic acid. The final product contains chromium propionate and sodium propionate.

EXAMPLE 6

Manganese Acetate

A preparation of manganese propionate is made by combining 114.95 grams of dry manganese carbonate, 300.30 grams of dry acetic acid, and 40.01 grams of sodium hydroxide. The mixture is heated to reflux with constant stirring. Water with some acetic acid is removed by fractional distillation. Heat is increased until the water and about 80 percent of the acetic acid liquid has been removed. Carbon dioxide is released through a vented condenser. The resulting composition of manganese acetate and sodium acetate in residual acetic acid is poured into a flat metal pan and placed in a freezer until cool. After cooling, the solution solidifies into a pink "glass". The "glass" is ground releasing the acetic acid. A white to slightly pink powder is collected containing manganese acetate and sodium acetate.

EXAMPLE 7

Cobalt Acetate

A preparation of cobalt acetate is made by combining 118.94 grams of dry cobalt carbonate, 300.30 grams of dry acetic acid and 40.01 grams of sodium hydroxide. The mixture is heated to reflux with constant stirring. Water with some acetic acid is removed by fractional distillation. Heat is increased until the water and about 80 percent of the acetic acid liquid has been removed. Carbon dioxide is released through a vented condenser. The resulting composition of cobalt acetate and sodium acetate in residual acetic acid is poured into a flat metal pan and placed in a freezer until cool. After cooling, the solution solidifies into a pink "glass". The "glass" is ground releasing the acetic acid. A purple powder is collected containing cobalt acetate and sodium acetate.

EXAMPLE 8

Chromium (III) Acetate

A preparation of chromium acetate is made by combining 151.99 grams of dry chromic oxide, 360.36 grams of dry acetic acid and 40.01 grams of sodium hydroxide. The mixture is heated to reflux with constant stirring. Water with some acetic acid is removed by fractional distillation. Heat is increased until the water and about 80 percent of the acetic acid has been removed. The resulting composition of chromium acetate and sodium acetate in residual acetic acid is poured into a flat metal pan and placed in a freezer until cool. After cooling, the solution solidifies into a "glass". The "glass" is ground releasing the acetic acid. The final product contains chromium acetate and sodium acetate.

The foregoing description and the examples are intended as illustrative and are not to be taken as limiting. Still other variations within the spirit and scope of this invention are possible and will readily present themselves to those skilled in the art.

We claim:

1. A catalyzed process for preparing a dry, particulate polyvalent metal cation carboxylate having a formula $M(CH_3(CH_2)_xCOO^-)_y$, wherein M is a polyvalent metal cation that is $Mn^{+2}$, $Co^{+2}$, or $Cr^{+3}$, x is zero or 1, and y is an integer equal to the cationic charge of M that comprises the steps of:

(a) admixing (i) a dry particulate polyvalent metal compound that is an oxide, hydroxide or carbonate of $Mn^{+2}$, $Co^{+2}$ or $Cr^{+3}$, (ii) an anhydrous carboxylic acid that is acetic or propionic acid and (iii) a catalytic agent, said admixing being at a relative molar ratio of about 1:2–10:0.01–3, respectively, and said admixing being carried out in the absence of added solvent or other diluent to form an exothermic reaction mixture that produces water as a product;

(b) maintaining said reaction mixture at reflux while continually removing said produced water and carboxylic acid for a time period sufficient to remove the water and about 80 percent of the unreacted carboxylic acid to form a composition of the catalyst and polyvalent metal cation carboxylate product in residual carboxylic acid;

(c) cooling and solidifying said product-containing solution;

(d) grinding said solid and separating said residual carboxylic acid from said product; and (e) collecting the product.

2. The process of claim 1 wherein the catalytic agent is a catalyst that is an alkali metal or alkaline earth metal salt of said carboxylic acid.

3. The process of claim 1 wherein the catalytic agent is a pre-catalyst that is an alkali metal or alkaline earth metal compound that reacts with said carboxylic acid to form an alkali metal or alkaline earth metal salt of said carboxylic acid as catalyst.

4. The process of claim 1 wherein the polyvalent metal compound is manganese carbonate.

5. The process of claim 1 wherein the polyvalent metal compound is cobalt carbonate.

6. The process of claim 1 wherein the polyvalent metal compound is chromic oxide.

7. The process of claim 1 wherein the carboxylic acid is propionic acid.

8. The process of claim 1 wherein the carboxylic acid is acetic acid.

9. The process of claim 3 wherein the pre-catalyst is sodium hydroxide.

10. The process of claim 2 wherein the catalyst is sodium propionate.

11. The process of claim 1 wherein the molar ratio of metal cation to carboxylic acid to pre-catalyst is about 1:5:1.

* * * * *